United States Patent
Kraut et al.

[11] Patent Number: 5,302,117
[45] Date of Patent: Apr. 12, 1994

[54] COIL-LESS UPRIGHTING SPRING

[75] Inventors: Jon Kraut, Trenton, N.J.; Paul Blanchette, Harwinton, Conn.; Timothy P. Kane, Holland, Pa.

[73] Assignee: Dentaurum, Inc., Newtown, Pa.

[21] Appl. No.: 58,493

[22] Filed: May 6, 1993

[51] Int. Cl.⁵ ............................... A61C 3/00
[52] U.S. Cl. .............................. 433/21; 433/18
[58] Field of Search .............. 433/21, 11, 18, 22

[56] References Cited

U.S. PATENT DOCUMENTS

| | | |
|---|---|---|
| 3,256,602 | 6/1966 | Broussard et al. ........... 433/21 X |
| 3,262,207 | 7/1966 | Kesling ........................... 433/21 X |
| 3,641,672 | 2/1972 | Kesling ........................... 433/21 |
| 3,793,730 | 2/1974 | Begg et al. ..................... 433/21 X |
| 4,580,976 | 4/1986 | O'Meara ......................... 433/21 |
| 4,842,514 | 6/1989 | Kesling ........................... 433/21 |
| 4,849,032 | 7/1989 | Kawaguchi ..................... 148/11.5 |
| 4,975,052 | 12/1990 | Spencer et al. ................ 433/21 |
| 5,017,132 | 5/1991 | Kesling ........................... 433/18 |
| 5,046,948 | 9/1991 | Miura .............................. 433/21 |
| 5,092,941 | 3/1992 | Miura .............................. 148/11.5 |
| 5,137,446 | 8/1992 | Yamauchi et al. ............. 433/20 |

Primary Examiner—Gene Mancene
Assistant Examiner—Cindy A. Cherichetti
Attorney, Agent, or Firm—Howson and Howson

[57] ABSTRACT

A coil-less wire-form orthodontic appliance for use with orthodontic brackets and archwire, installed in the mouth of a patient, for uprighting teeth.

14 Claims, 2 Drawing Sheets

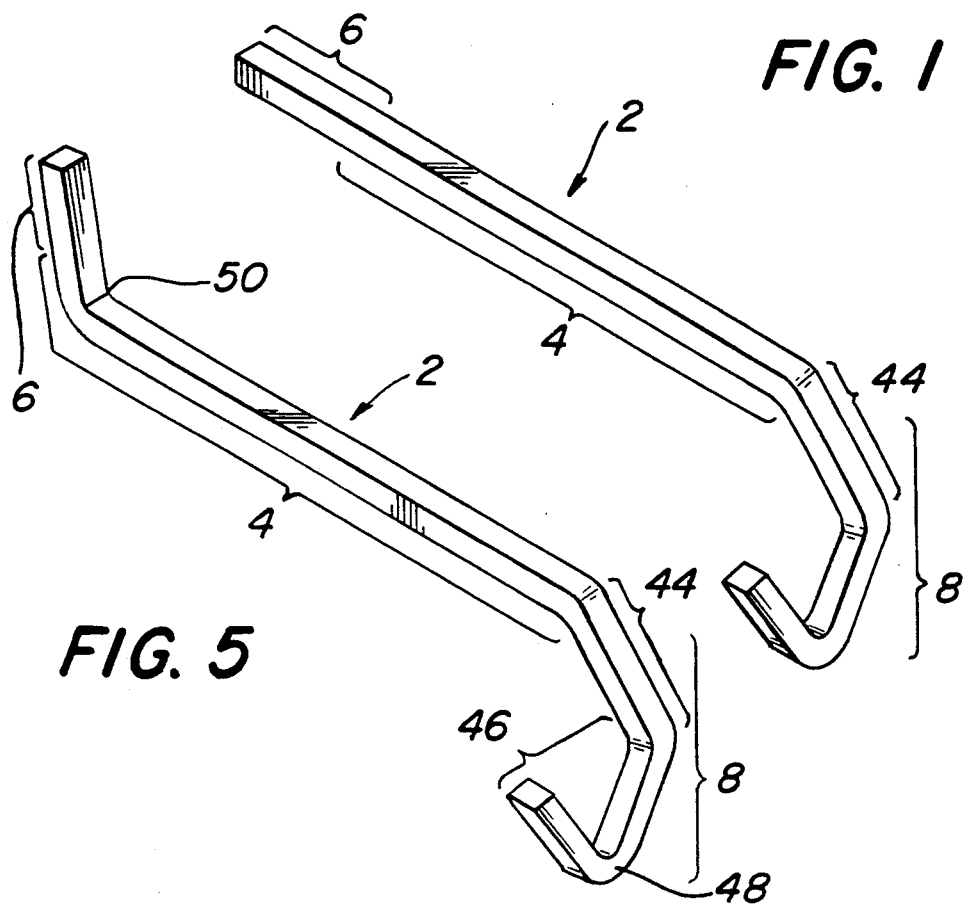
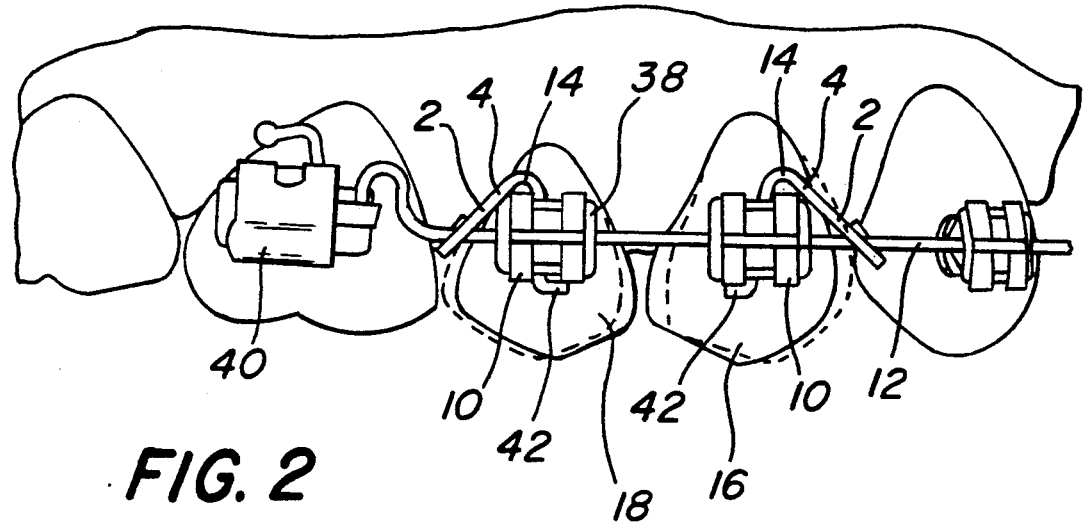

5,302,117

COIL-LESS UPRIGHTING SPRING

FIELD OF THE INVENTION

The present invention relates to an orthodontic auxiliary for use with a bracket appliance and archwire for uprighting a tooth, repositioning the roots, and more particularly, the present invention relates to a coil-less memory shaped wire-form which exerts uprighting forces on a tooth when the wire-form is properly connected between an orthodontic bracket and archwire.

BACKGROUND OF THE INVENTION

In the practice of orthodontics, an orthodontist may use bracket appliances and an archwire to move and position teeth in a patient's mouth. The brackets are fixed to several teeth, generally, to all of the patient's anterior teeth and to the first molars. Archwires are loosely pinned to the brackets to provide archform and the function of leveling the teeth.

Auxiliary appliances can be used in conjunction with the brackets and archwires to apply rotating, tipping, and torquing forces to an individual tooth in an effort to correct the position of the tooth in relation to the other teeth in the patient's mouth. Rotating forces will cause a tooth to rotate about its long axis. Tipping forces will cause the movement of a tooth about its longitudinal axis in a mesial-distal direction. Torquing forces will cause the movement of a tooth about its longitudinal axis in buccal-lingual direction.

One such auxiliary appliance is an uprighting spring. Generally, an uprighting spring connects between the bracket and archwire, and applies one or a combination of tipping and rotating forces to any tooth. The wire-form of conventional uprighting springs have a relatively complex structure with many bends, twists and turns. The conventional uprighting spring incorporates a helix structure as a means for delivering force to the tooth.

Several disadvantages are inherent in the helix force generator and complex wire-form structure. The shape of the complex structure, the helix in particular, provides an ideal place for the build up and retention of plaque. It is common for a patient to experience gingival irritation near the location of the helix. Mechanically, due to the environment in which the helix is located, a stainless steel uprighting spring may lose force with time and may need to be replaced or reactivated. This results in the patient requiring more appointments and chair time with the orthodontist, over and above the initial chair time required to install the complex structured uprighting spring.

SUMMARY OF THE INVENTION

Accordingly, it is an object of the present invention to provide an improved uprighting spring having a relatively simple structure for use as an auxiliary appliance with orthodontic brackets and an archwire.

Another object of the present invention is to provide an uprighting spring that does not utilize a helix as its force generator, and that eliminates the plaque retentive nature and tendency for gingival irritation associated with the use of a helix.

Still another object of the present invention is to provide a coil-less uprighting spring with a force generator that can deliver constant force values, without requiring reactivation, thereby reducing patient chair time.

Still another object of the present invention is to provide an uprighting spring which an orthodontist can easily insert and remove, thereby further reducing patient chair time.

Briefly, these and other objects of the present invention are achieved by an orthodontic uprighting wire-form appliance for use with a standard archwire and bracket assembly. The bracket has an archwire slot for receiving the archwire and a recess for receiving the wire-form appliance. The wire-form appliance has an intermediate portion formed into a predetermined shape of a material having shape-memory. A tail portion extends from the intermediate portion and is capable of being bent for locking the appliance to the bracket. Additionally, a crimpable tube can be placed onto the tail portion with a locking mechanism to prevent dislodging. The intermediate and tail portions lie in a common plane with no helix-like structure. A hook having a bight portion extends from the intermediate portion, remote from the tail portion, for engaging the archwire. The hook extends lateral to the plane of the intermediate and tail portions. When the tail portion is locked to the bracket and the hook is engaged with the archwire, the intermediate portion tends to return to a predetermined memorized shape causing uprighting forces to be applied to the tooth, which places a moment of force onto the roots creating the desired movement.

BRIEF DESCRIPTION OF THE DRAWINGS

The foregoing and other objects, features and advantages of the present invention should become apparent from the following description when taken in conjunction with the accompanying drawings, wherein:

FIG. 1 is a perspective view of an embodiment of a coil-less uprighting wire-form orthodontic appliance according to the present invention;

FIG. 2 is an elevational view illustrating several teeth of a patient with orthodontic brackets, archwire and two uprighting appliances installed according to the present invention;

FIG. 5 is a perspective view of an alternate embodiment of a coil-less uprighting wire-form orthodontic appliance according to the present invention.

DESCRIPTION OF THE PREFERRED EMBODIMENT

Figure 3:
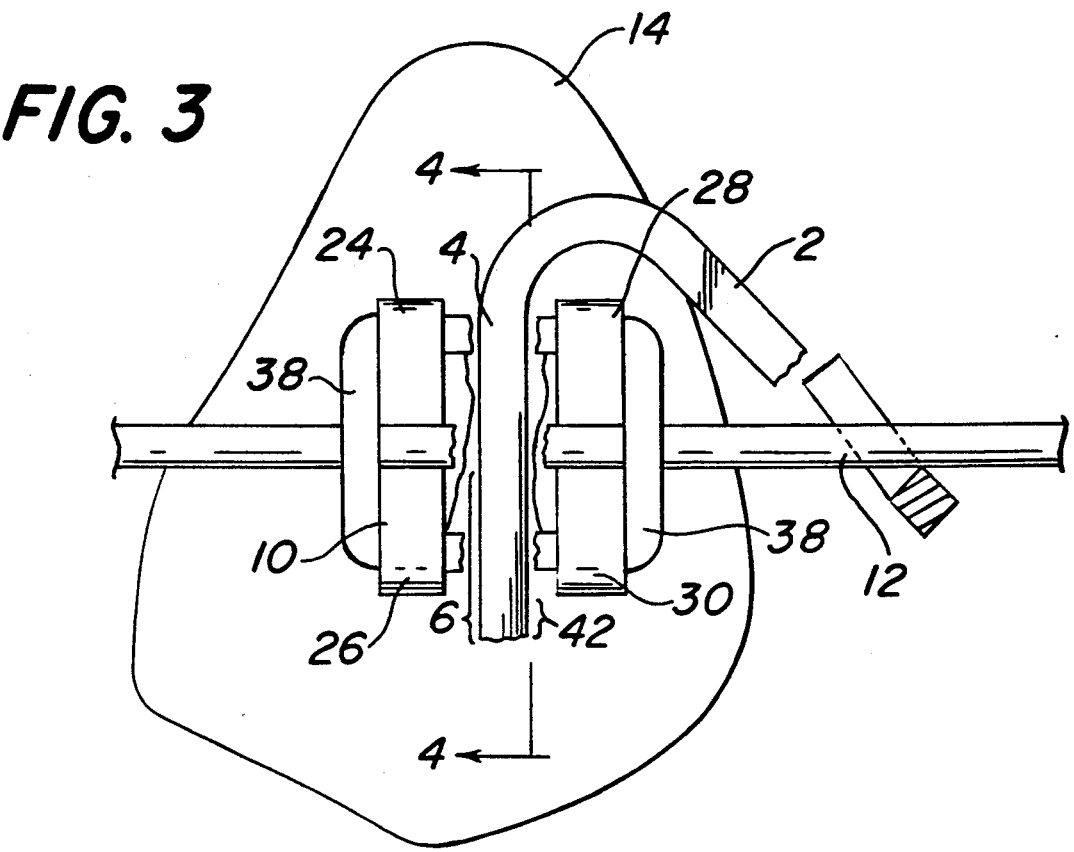
FIG. 3 is a fragmentary elevational view of an installed uprighting appliance in combination with a bracket and archwire on a tooth of a patient according to the present invention.

Referring now to the drawings wherein like reference characters designate like or corresponding parts throughout the several views, there is illustrated in FIG. 1 an uprighting wire-form appliance 2. The uprighting wire-form appliance 2 can be used with a typical orthodontic bracket and archwire assembly to apply uprighting forces to a tooth.

Figure 4:
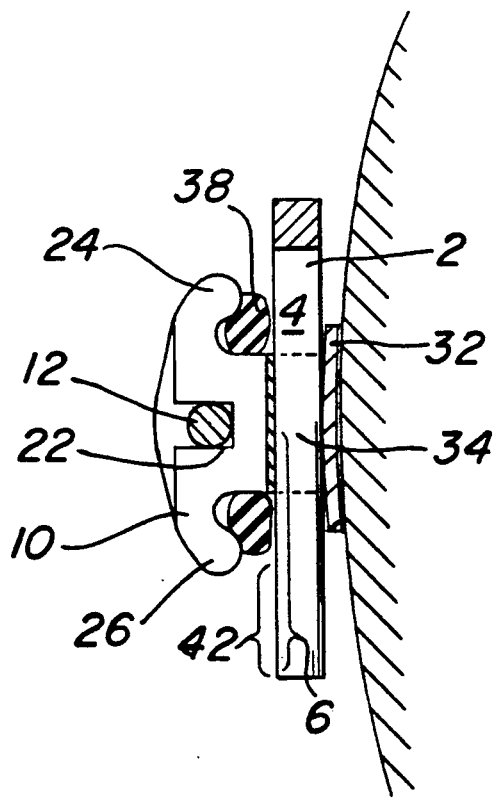
FIG. 4 is a cross-sectional view of a bracket and uprighting appliance along the line 4——4 of FIG. 3.

FIGS. 2, 3 and 4 illustrate a typical bracket 10 and archwire 12 which can be used in conjunction with the uprighting wire-form appliance 2. The bracket 10 has a base 32 which is secured to the surface of a tooth by means of an adhesive (not shown). The bracket 10 includes a twin tie wing assembly 36 which is integral with the base 32 The twin tie wing assembly 36 forms a horizontal archwire slot 22 and has extending tie wing members 24, 26, 28, and 30. A recess 34 is formed between the tie wing assembly 36 and the base 32 for purposes to be discussed.

A plurality of brackets 10 are interconnected in a well-known manner by the archwire 12. The archwire 12 fits into the archwire slot 22 of each bracket 10. The archwire 12 is secured in each bracket 10 by an elastomeric band 38 which is installed around the twin tie wing assembly 36 and is held in place by extending tie wing members 24, 26, 28, and 30. The ends of the archwire 12 are secured to an ending bracket 40 which allows the orthodontist to tighten or loosen the archwire 12.

The uprighting wire-form appliance 2 has three separate functioning sections: an intermediate portion 4, a tail portion 6 extending from one end of the intermediate portion 4, and a hook 8 extending from the intermediate portion 4 remote from the tail portion 6.

The purpose of the intermediate portion 4 is to cooperate with the bracket 10 and archwire 12 to generate the uprighting forces which are applied to the tooth. To this end, intermediate portion 4 is formed into a predetermined shape of a material having shape memory properties. As illustrated in FIG. 1, the predetermined memorized shape of the intermediate portion 4 is straight, but other non-helical shapes may be utilized, eg. various angles or series of bends. As shown in FIGS. 2 and 3, when the uprighting wire-form appliance 2 is installed on a tooth 16 and engaged with the bracket 10 and archwire 12, a bend 14 will occur in the intermediate portion 4. The shape memory of the intermediate portion 4, in returning to its straight shape, will cause the intermediate portion 4 to apply forces to the bracket 10 to displace the tooth 16 for uprighting the tooth 16.

The purpose of the tail portion 6 is to lock the uprighting wire-form appliance 2 to the bracket 10. The tail portion 6 and a portion of the intermediate wire-form portion 4 are inserted into the vertical recess 34 in the bracket 10. As shown in FIG. 2, a terminal end section 42 of the tail portion 6 extends beyond the edge of the bracket 10. The terminal end section 42 is bent, or cinched back, along the periphery of bracket 10, thereby locking the uprighting wire-form appliance 2 to the bracket 10. Alternatively, equivalent means for locking the tail portion 6 to the bracket can be used, for instance, by crimping a stop (not shown) onto the terminal end portion 42 of the wire-form 2.

The purpose of the hook 8 is to engage the archwire 12 such that the uprighting wire-form appliance is secured between the bracket 10 and the archwire 12, and the bend 14 is formed in the intermediate portion 4. The hook 8 has a first section 44 which extends at an obtuse angle from the intermediate portion 4. A return section 46 extends from the first section 44 for forming a wire engageable bight portion 48. The orientation of the hook 8 and the part of the jaw in which the tooth is located, ie. upper or lower, right or left, will determine whether the uprighting wire-form appliance 2 can be used to upright a tooth toward a mesial direction or toward a distal direction. For instance, tooth 18 of FIG. 2 is shown being uprighted in a mesial direction, while tooth 16 is shown being uprighted in a distal direction, the dotted lines representing the tooth position prior to being uprighted.

The structure of the uprighting wire-form appliance 2 formed by the intermediate portion 4, tail portion 6, and hook 8 has a minimum of bends, and lacks the helical configuration of the prior art and its disadvantages. The intermediate portion 4, the tail portion 6, and the first section 44 of the hook 8 are coplanar, thereby minimizing buccal protrusions. The return section 46 of hook 8 is formed lateral to the plane of the intermediate portion 4, tail portion 6, and first section 44 of the hook 8, and is the only non-coplanar structure.

The entire uprighting wire-form appliance 2, or at least the intermediate portion 4, is made of a material having shape memory and corrosion-resistance properties. For instance, the entire uprighting wire-form appliance 2 can be made from a nickel-titanium alloy. As the best mode, the present invention utilizes an alloy of 55% nickel and 45% titanium. Although other equivalent alloys can be used, this alloy, formed in a predetermined shape consistent with that of the present invention, generates the proper amount of force to upright a tooth when installed between a bracket 10 and archwire 12.

Some embodiments of the present invention require that the terminal end section 42 of the tail portion 6 be annealed. This is necessary if the terminal end section 42 is to be cinched back along the periphery of a bracket. In such case, the terminal end section 42 cannot exhibit shape memory properties. Therefore, the terminal end section 42 is annealed so that the annealed terminal end section 42 can be bent, or unbent, only by the orthodontist using special tools.

The predetermined shape of the intermediate and tail portions, 4 and 6, can be altered to change the forces exerted on a tooth. As illustrated in FIG. 5, in one embodiment of the present invention the intermediate and tail section, 4 and 6, is formed into a predetermined shape from a shape memory material and includes a bend 50. The bend 50 of the illustrated predetermined shape will cause an increase in the force generated by the uprighting wire-form appliance 2 as it attempts to return to its predetermined shape. The best mode for uprighting a premolar tooth consistent with the present invention is to have a 135° bend 50 in the predetermined shape of the intermediate and tail portions, 4 and 6. For uprighting in a mesial or distal direction, and depending on which part of the jaw the tooth is located, the bend 50 should extend appropriately either on the same or opposite side of the intermediate portion 4 with that of the first section 44 of the hook 8.

The shape of the cross-section of the uprighting wire-form appliance 2 can also provide a useful function. The cross-section illustrated in FIGS. 1–5 is rectangular or square. With this cross-section, as shown in FIG. 3, the uprighting wire-form appliance fits snugly in the recess 34 of the bracket 10 in a vertical direction. Since the uprighting wire-form appliance 2 cannot rotate within the bracket, the uprighting wire-form appliance delivers both tipping and rotating forces to the tooth 16. Alternatively, the cross-section of the uprighting wire-form appliance 2 can be oval or circular (not shown) to allow slight rotation of the uprighting wire-form appliance inside the bracket 10. The slight rotation allowed by the circular cross-section will deliver mostly tipping forces. Preferably, the wire has a cross-sectional area in a range of about .0002009 to about .000576 square inches, and provides a flexural modulus, or bending stiffness, of about 50 grams to about 300 grams, and tensile strength in a range of about 120,000 psi to about 215,000 psi.

It will be understood, of course, that various changes may be made by those skilled in the art within the principle and scope of the invention as expressed in the appended claims.

We claim:

1. An orthodontic uprighting wire-form appliance for use with an archwire and bracket to effect mesial/distal root inclination, said bracket having an archwire slot for receiving said archwire and a recess for receiving said wire-form appliance, said wire-form appliance comprising:

an intermediate portion formed into a predetermined shape of a material having shape-memory;

a tail portion, extending from said intermediate portion, capable of being bent for locking said appliance to said bracket;

a hook having a bight portion, remote from said tail portion, for engaging said archwire, said hook extending lateral to said plane; and said intermediate and tail portions lying in a common plane and extending in a substantially direct path between the archwire and bracket;

whereby, when said tail portion is locked to said bracket and said hook is engaged with said archwire, said intermediate portion tends to return to a predetermined memorized shape causing uprighting forces to be applied to said tooth for effecting either mesial or distal root movement.

2. An orthodontic uprighting wire-form appliance according to claim 1, wherein said predetermined memorized shape of said intermediate and tail portions is straight.

3. An orthodontic uprighting wire-form appliance according to claim 1, wherein said predetermined memorized shape of said intermediate and tail portions includes a bend at an obtuse included angle.

4. An orthodontic uprighting wire-form appliance according to claim 3, wherein said obtuse angle of said bend is about 135°.

5. An orthodontic uprighting wire-form appliance according to claim 1, wherein said shape memory material of said wire-form appliance is a nickel titanium alloy.

6. An orthodontic uprighting wire-form appliance according to claim 5, wherein said tail portion has an end section located remote from said intermediate portion and annealed to remove shape memory from said end section of said tail portion.

7. An orthodontic uprighting wire-form appliance according to claim 6, wherein said wire-form appliance has a rectangular cross section.

8. An orthodontic assembly for uprighting a tooth to effect mesial/distal root inclination, said assembly comprising a bracket adapted to be affixed to a tooth, said bracket having an archwire slot for receiving an archwire and a recess transverse to said slot, and a wire-form appliance engageable with said archwire and said bracket recess, said appliance comprising:

an intermediate portion formed into a predetermined shape of a material having shape-memory;

a tail portion, extending from said intermediate portion, capable of being bent for locking said appliance to said bracket;

a hook having a bight portion, remote from said tail portion, for engaging said archwire, said hook extending lateral to said plane; and said intermediate and tail portions lying in a common plane and extending in a substantially direct path between the archwire and bracket;

whereby, when said tail portion is locked to said bracket and said hook is engaged with said archwire, said intermediate portion tends to return to a predetermined memorized shape causing uprighting forces to be applied to said tooth for effecting either mesial or distal root movement.

9. An orthodontic assembly according to claim 8, wherein said tail portion has a crimped stop locking said tail portion to said bracket after said tail portion has been inserted through and partially extended beyond said bracket recess.

10. An orthodontic assembly according to claim 9, wherein said intermediate portion flexes in the region between said tail portion and said hook when operatively engaged with said bracket and said archwire.

11. A wire-form for use with an orthodontic archwire and a bracket to upright a tooth to effect mesial/distal root inclination, said bracket having a buccal archwire slot for receiving said archwire and a vertically extending lingual recess for receiving said wire-form, said wire-form comprising:

a straight intermediate portion;

a straight tail portion extending from said intermediate portion and having a terminal end section remote from said intermediate portion, said tail portion capable of being inserted through and partially extended beyond said recess so that said terminal end section can be bent to lock said tail portion to said bracket; and a hook remote from said tail portion for engaging said archwire, said hook having a first section extending at an obtuse angle from said intermediate portion coplanar with said intermediate and tail portions, and a return section forming a wire-engageable bight portion lateral to said intermediate and tail portions;

said wire-form being made from a 55% nickel and 45% titanium shape memory alloy with said terminal end section of said tail portion being annealed;

said straight intermediate and tail portions extending in a substantially direct path between the archwire and bracket;

whereby, when said tail portion is locked to said bracket and said hook is engaged with said archwire, said intermediate portion tends to return to a predetermined memorized shape and causes uprighting forces to be applied to said tooth for effecting either mesial or distal root movement.

12. A wire-form according to claim 11, wherein said tail portion extends at an obtuse angle with respect to said intermediate portion.

13. A wire-form according to claim 11 having a cross-sectional area in a range of about 0.0002009 to about 0.000576 square inches.

14. A wire-form according to claim 11 having a bending stiffness in a range of about 50 to about 300 grams and a tensile strength in a range of about 120,000 to about 215,000 psi.

* * * * *